(12) United States Patent
Daba

(10) Patent No.: US 11,246,784 B2
(45) Date of Patent: Feb. 15, 2022

(54) WALKING TRAINING APPARATUS AND METHOD OF CONTROLLING THE SAME

(71) Applicant: TOYOTA JIDOSHA KABUSHIKI KAISHA, Toyota (JP)

(72) Inventor: Hiroaki Daba, Nisshin (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 722 days.

(21) Appl. No.: 15/839,936

(22) Filed: Dec. 13, 2017

(65) Prior Publication Data
US 2018/0221235 A1  Aug. 9, 2018

(30) Foreign Application Priority Data
Feb. 8, 2017 (JP) .............................. JP2017-021086

(51) Int. Cl.
*A61H 1/02* (2006.01)
*A61H 3/00* (2006.01)
(Continued)

(52) U.S. Cl.
CPC ........... *A61H 1/0262* (2013.01); *A61B 5/103* (2013.01); *A61H 1/024* (2013.01); *A61H 1/0229* (2013.01); *A61H 1/0237* (2013.01); *A61H 1/0244* (2013.01); *A61H 3/00* (2013.01); *A61H 3/008* (2013.01); *A63B 21/00181* (2013.01); *A63B 21/4011* (2015.10); *A63B 22/02* (2013.01); *A63B 22/0235* (2013.01);
(Continued)

(58) Field of Classification Search
CPC ........ A61H 1/0262; A61H 3/00; A61H 3/008; A63B 23/10
See application file for complete search history.

(56) References Cited

U.S. PATENT DOCUMENTS

2011/0312473 A1\* 12/2011 Chu ................... A63B 69/0064
482/54
2015/0342820 A1\* 12/2015 Shimada ............ A63B 69/0028
482/69
(Continued)

FOREIGN PATENT DOCUMENTS

CN  101862255 B   9/2011
EP  2 949 365 A1  12/2015
(Continued)

*Primary Examiner* — Michael J Tsai
(74) *Attorney, Agent, or Firm* — Oblon, McClelland, Maier & Neustadt, L.L.P.

(57) ABSTRACT

A walking training apparatus includes: a treadmill; a walking assistance apparatus configured to be mounted on a leg part of a user and assist the user's walking; a first pulling means for pulling at least one of the walking assistance apparatus and the leg part of the user upward and frontward; a second pulling means for pulling at least one of the walking assistance apparatus and the leg part of the user upward and rearward; and control means for controlling, while the treadmill is not being operated, pulling forces of the first pulling means and the second pulling means in such a way that the direction of a resultant pulling force, which is a resultant force of the pulling force of the first pulling means and the pulling force of the second pulling means, is changed rearward compared to a case in which the treadmill is being operated.

2 Claims, 9 Drawing Sheets

(51) Int. Cl.

| | | |
|---|---|---|
| *A61B 5/103* | (2006.01) | |
| *A63B 22/02* | (2006.01) | |
| *G06K 9/00* | (2022.01) | |
| *A63B 21/00* | (2006.01) | |
| *A63B 69/00* | (2006.01) | |
| *A63B 24/00* | (2006.01) | |
| *A63B 23/04* | (2006.01) | |
| *A63B 22/00* | (2006.01) | |

(52) U.S. Cl.
CPC .......... *A63B 23/04* (2013.01); *A63B 24/0087* (2013.01); *A63B 69/0028* (2013.01); *A63B 69/0057* (2013.01); *G06K 9/00342* (2013.01); *A61H 2003/007* (2013.01); *A61H 2201/1215* (2013.01); *A61H 2201/165* (2013.01); *A61H 2201/1621* (2013.01); *A61H 2201/1635* (2013.01); *A61H 2201/1642* (2013.01); *A61H 2201/1664* (2013.01); *A61H 2201/1671* (2013.01); *A61H 2201/501* (2013.01); *A61H 2201/5007* (2013.01); *A61H 2201/5043* (2013.01); *A61H 2201/5061* (2013.01); *A61H 2201/5069* (2013.01); *A61H 2201/5071* (2013.01); *A61H 2201/5097* (2013.01); *A61H 2203/0406* (2013.01); *A61H 2205/10* (2013.01); *A61H 2205/102* (2013.01); *A61H 2205/106* (2013.01); *A63B 22/025* (2015.10); *A63B 69/0062* (2020.08); *A63B 2022/0094* (2013.01); *A63B 2024/0093* (2013.01); *A63B 2220/16* (2013.01); *A63B 2220/54* (2013.01); *A63B 2220/803* (2013.01)

(56) References Cited

U.S. PATENT DOCUMENTS

| | | | |
|---|---|---|---|
| 2016/0051859 | A1* | 2/2016 | Nakashima ...... A63B 21/00181 482/4 |
| 2017/0027803 | A1* | 2/2017 | Agrawal ................ A61B 5/224 |
| 2017/0035642 | A1 | 2/2017 | Sugata |
| 2017/0049660 | A1 | 2/2017 | Sugata |
| 2017/0071813 | A1 | 3/2017 | Sugata |

FOREIGN PATENT DOCUMENTS

| | | |
|---|---|---|
| JP | 2015-223294 | 12/2015 |
| JP | 2017-35220 | 2/2017 |
| JP | 2017-38658 | 2/2017 |
| JP | 2017-51464 | 3/2017 |
| WO | WO 2015/164421 A1 | 10/2015 |

* cited by examiner

WALKING TRAINING APPARATUS AND METHOD OF CONTROLLING THE SAME

CROSS REFERENCE TO RELATED APPLICATIONS

This application is based upon and claims the benefit of priority from Japanese patent application No. 2017-021086, filed on Feb. 8, 2017, the disclosure of which is incorporated herein in its entirety by reference.

BACKGROUND

The present invention relates to a walking training apparatus used by a user to perform walking training and a method of controlling the same.

A walking training apparatus by which a user performs walking training on a treadmill with a walking assistance apparatus that assists user's walking attached to his/her leg part has been known (see, for example, Japanese Unexamined Patent Application Publication No. 2015-223294).

The walking training apparatus disclosed in Japanese Unexamined Patent Application Publication No. 2015-223294 includes, besides the treadmill and the walking assistance apparatus described above, a first pulling means for pulling the leg part of the user upward and frontward and a second pulling means for pulling the leg part of the user upward and rearward. The walking training apparatus controls pulling forces of the first pulling means and the second pulling means in such a way that a resultant pulling force is directed upward in order to reduce a load applied to the leg part of the user.

SUMMARY

Incidentally, in recent walking training, the user may perform a stepping operation on site while the treadmill is in a non-operating state, and then after learning the walking rhythm through the stepping operation, the user may operate the treadmill to perform a walking operation.

It is assumed that the user performs the walking operation in a state in which the treadmill is in an operating state in the walking training apparatus disclosed in Japanese Unexamined Patent Application Publication No. 2015-223294. It is not assumed, in this document, that the user may perform the stepping operation in a state in which the treadmill is in the non-operating state.

Therefore, when the user performs the stepping operation while the treadmill is in the non-operating state in the walking training apparatus disclosed in Japanese Unexamined Patent Application Publication No. 2015-223294, the user needs to perform the stepping operation while moving the leg part backward in order to prevent him/her from moving forward in accordance with the stepping operation, which may be a burden on the user.

The present invention has been made in view of the aforementioned circumstances and provides a walking training apparatus capable of suppressing the possibility that a burden is imposed on the user while the user is performing the stepping operation and a method of controlling the same.

A walking training apparatus according to one aspect of the present invention includes:
a treadmill;
a walking assistance apparatus configured to be mounted on a leg part of a user and assist the user's walking;
a first pulling means for pulling at least one of the walking assistance apparatus and the leg part of the user on which the walking assistance apparatus is mounted upward and frontward;
a second pulling means for pulling at least one of the walking assistance apparatus and the leg part of the user on which the walking assistance apparatus is mounted upward and rearward; and
a control means for controlling pulling forces of the first pulling means and the second pulling means in such a way as to reduce a load applied to the leg part of the user on which the walking assistance apparatus is mounted, in which
the control means controls, while the treadmill is not being operated, pulling forces of the first pulling means and the second pulling means in such a way that the direction of a resultant pulling force, which is a resultant force of the pulling force of the first pulling means and the pulling force of the second pulling means, is changed rearward compared to a case in which the treadmill is being operated.

A method of controlling a walking training apparatus according to one aspect of the present invention is a method of controlling a walking training apparatus, the walking training apparatus including:
a treadmill;
a walking assistance apparatus configured to be mounted on a leg part of the user and assist the user's walking;
a first pulling means for pulling at least one of the walking assistance apparatus and the leg part of the user on which the walking assistance apparatus is mounted upward and frontward; and
a second pulling means for pulling at least one of the walking assistance apparatus and the leg part of the user on which the walking assistance apparatus is mounted upward and rearward, the method including:
controlling, while the treadmill is not being operated, pulling forces of the first pulling means and the second pulling means in such a way that the direction of a resultant pulling force, which is a resultant force of the pulling force of the first pulling means and the pulling force of the second pulling means, is changed rearward compared to a case in which the treadmill is being operated.

According to the aspects of the present invention, it is possible to provide a walking training apparatus capable of suppressing the possibility that a burden is imposed on the user while the user is performing the stepping operation and a method of controlling the same.

The above and other objects, features and advantages of the present invention will become more fully understood from the detailed description given hereinbelow and the accompanying drawings which are given by way of illustration only, and thus are not to be considered as limiting the present invention.

DESCRIPTION OF EMBODIMENTS

Figure 1:
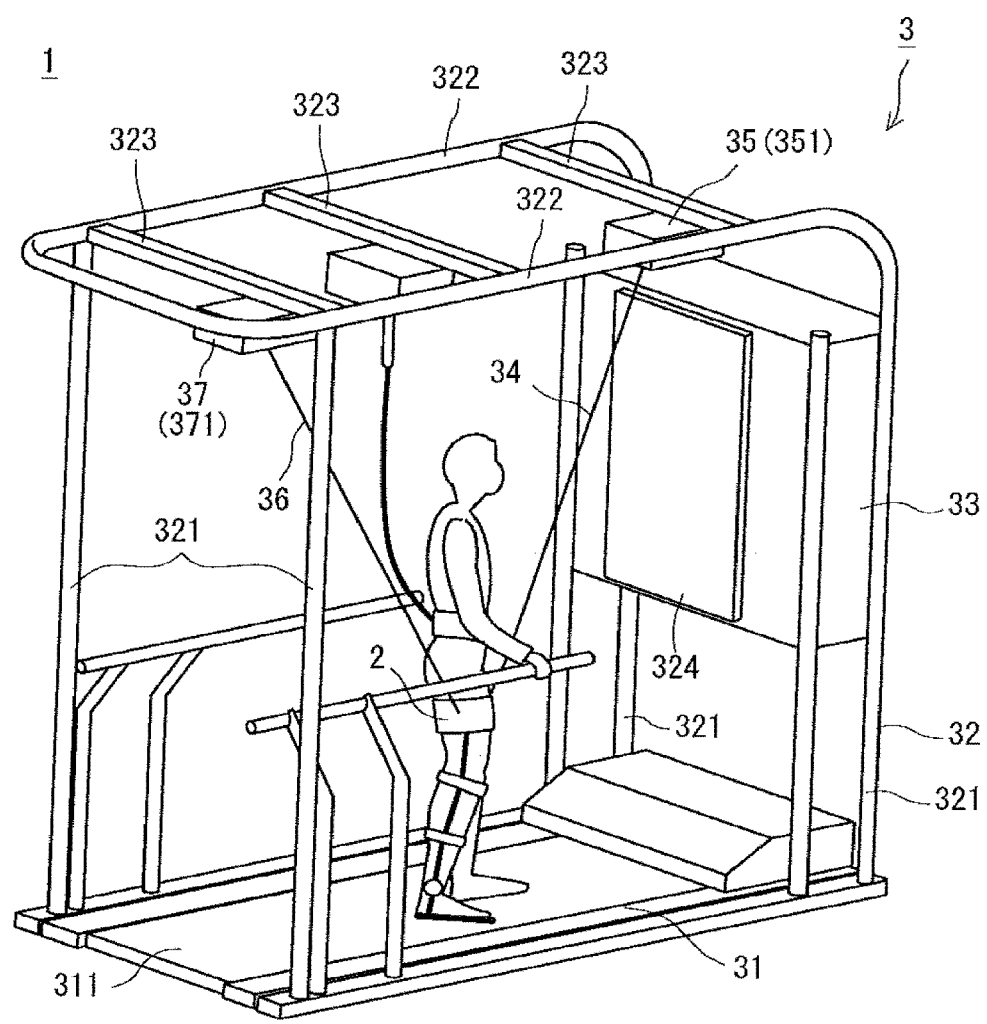
FIG. 1 is a perspective view showing one example of a schematic external configuration of a walking training apparatus according to an embodiment of the present invention.

A specific embodiment of the present invention is explained hereinafter in detail with reference to the drawings. In the drawings, the same or corresponding elements are denoted by the same reference signs, and repetitive descriptions will be avoided as necessary for clarity of explanation.

FIG. 1 is a perspective view showing one example of a schematic external configuration of a walking training apparatus 1 according to an embodiment of the present invention. The walking training apparatus 1 is an apparatus that is used to perform, for example, walking training for a user such as a patent suffering from hemiplegia. The walking training apparatus 1 includes a walking assistance apparatus 2 mounted on an affected leg (in FIG. 1, the right leg) of the leg parts of the user and a training apparatus 3 which performs the walking training for the user.

Figure 2:
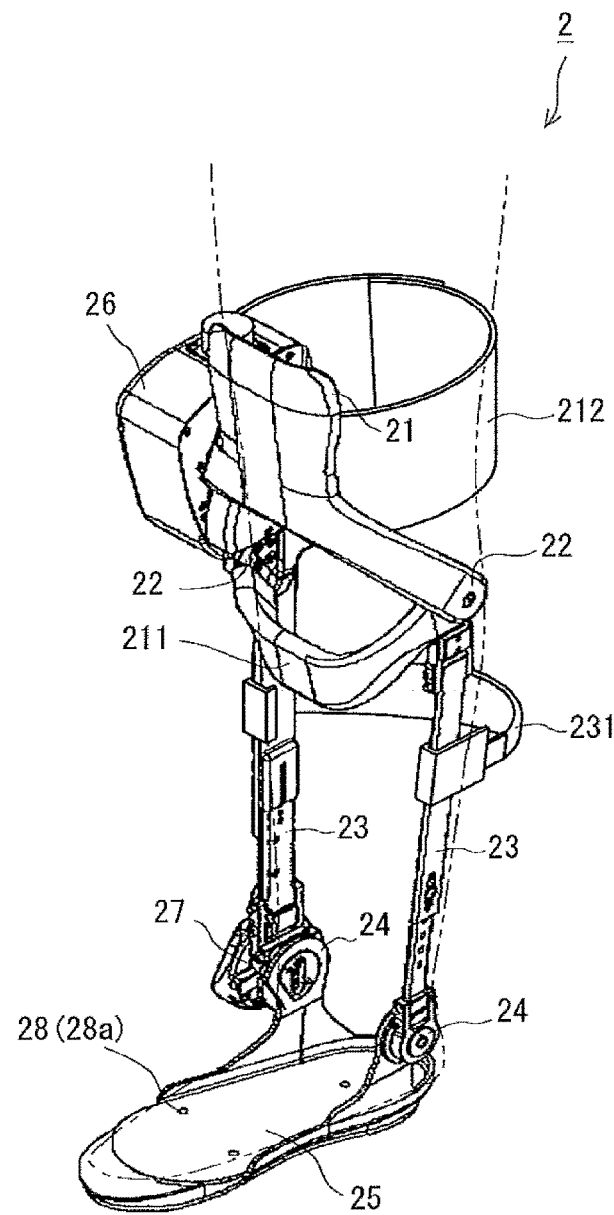
FIG. 2 is a perspective view showing one example of a schematic external configuration of a walking assistance apparatus according to the embodiment of the present invention.

The walking assistance apparatus 2 is mounted on, for example, the affected leg of the user and assists user's walking (FIG. 2). The walking assistance apparatus 2 includes an upper thigh frame 21, a lower thigh frame 23 coupled to the upper thigh frame 21 via a knee joint part 22, a sole frame 25 coupled to the lower thigh frame 23 via an ankle joint part 24, a motor unit 26 that rotationally drives the knee joint part 22, and an adjustment mechanism 27 that adjusts a movable range of the ankle joint part 24. The structure of the walking assistance apparatus 2 is merely one example and the structure thereof is not limited to the one stated above. The walking assistance apparatus 2 may include, for example, a motor unit that rotationally drives the ankle joint part 24.

The sole frame 25 is provided with a sole load detection unit 28 formed of a plurality of load sensors 28a that detect the load that the sole of the user receives. In FIG. 2, a pair of load sensors 28a are arranged on the tip side of the sole frame 25 and a pair of load sensors 28a are arranged on the heel side thereof. The number of load sensors 28a and the location of the load sensors 28a are not limited as long as they are arranged in such a manner that the center of the load of the sole can be accurately obtained.

The upper thigh frame 21 is fixed to the upper thigh part of the affected leg of the user and the lower thigh frame 23 is fixed to the lower thigh part of the affected leg of the user. The upper thigh frame 21 is provided with, for example, an upper thigh equipment 212 to fix the upper thigh part. It is therefore possible to prevent the walking assistance apparatus 2 from being deviated in the horizontal direction or the vertical direction from the affected leg of the user.

The upper thigh frame 21 is provided with a first frame 211 which is formed in a horizontal long shape and extends in the horizontal direction to connect a wire 34 of a first pulling unit (first pulling means) 35. The lower thigh frame 23 is provided with a second frame 231 which is formed in a horizontal long shape and extends in the horizontal direction to connect a wire 36 of a second pulling unit (second pulling means) 37.

The aforementioned structure of the walking assistance apparatus 2 is merely one example and is not limited to the one described above. A desired walking assistance apparatus mounted on the affected leg of the user and capable of assisting the user's walking may be employed as the walking assistance apparatus 2.

The training apparatus 3 includes a treadmill (in the drawings, the treadmill may be indicated by "TM") 31, a frame body 32, a control apparatus 33, the first pulling unit 35, and the second pulling unit 37. The treadmill 31 includes a rotatable ring-shaped belt 311. When performing walking training, the user stands on the belt 311 and performs a walking operation in a state in which the treadmill 31 is being operated (i.e., a state in which the belt 311 is being rotated) and performs a stepping operation in a state in which the treadmill 31 is not being operated (i.e., a state in which the rotation of the belt 311 is being stopped).

The frame body 32 includes two pairs of column frames 321 which are installed on the treadmill 31, a pair of front and rear frames 322 which are connected to the respective column frames 321 and extend in the front-back direction, and three right and left frames 323 which are connected to the front and rear frames 322 and extend in the horizontal direction. The aforementioned structure of the frame body 32 is not limited to the one described above. The frame body 32 may have any frame structure as long as the first and second pulling units 35 and 37 can be appropriately fixed to the frame body 32.

The right and left frame 323 on the front side is provided with the first pulling unit 35 which pulls the wire 34 upward and frontward. The right and left frame 323 on the rear side is provided with the second pulling unit 37 which pulls the wire 36 upward and rearward.

The first pulling unit 35 includes, for example, a mechanism which winds and rewinds the wire 34, a forward motor 351 which drives this mechanism and the like. The second pulling unit 37 includes, for example, a mechanism which winds and rewinds the wire 36, a backward motor 371 which drives this mechanism and the like. One end of the wire 34 pulled by the first pulling unit 35 is connected to the first frame 211 of the walking assistance apparatus 2 and one end of the wire 36 pulled by the second pulling unit 37 is connected to the second frame 231 of the walking assistance apparatus 2. The first pulling unit 35 pulls the walking assistance apparatus 2 upward and frontward via the wire 34. The second pulling unit 37 pulls the walking assistance apparatus 2 upward and rearward via the wire 36. The first pulling unit 35 and the second pulling unit 37 adjust the pulling forces of the wires 34 and 36 by adjusting relief torque of the forward motor 351 and that of the backward motor 371.

While the aforementioned first pulling unit 35 and second pulling unit 37 connect the wires 34 and 36 to the first frame 211 and the second frame 231 and the affected leg of the user is indirectly pulled via the walking assistance apparatus 2, this connection is merely one example. A connection in which the wire 34 of the first pulling unit 35 and the wire 36 of the second pulling unit 37 are connected to the upper thigh equipment 212 and the affected leg of the user is directly pulled may be employed. Alternatively, a connection in which the wire 34 of the first pulling unit 35 and the wire 36 of the second pulling unit 37 are connected to both the first frame 211 and the second frame 231 and the upper thigh equipment 212 and the affected leg of the user is pulled directly and indirectly via the walking assistance apparatus 2 may be employed.

The frame body 32 is provided with a display unit 324 that displays information such as training instructions, training menu, training information (walking speed, biological information etc.)

The control apparatus 33 controls each of the pulling forces of the first pulling unit 35 and the second pulling unit 37, the operation of the treadmill 31, and the operation of the walking assistance apparatus 2. The control apparatus 33 includes a processor such as a Central Processing Unit (CPU) and a storage unit. The processor executes the program stored in the storage unit, whereby the processing of the control apparatus 33 is achieved. That is, the program stored in the storage unit of the control apparatus 33 includes a code for causing the processor to execute the processing in the control apparatus 33. The storage unit is configured to include, for example, a storage apparatus capable of storing the aforementioned program and various kinds of information to be used for processing in the processor. The storage apparatus may be at least one arbitrary storage apparatus among storage apparatuses such as a memory and a hard disc.

Further, the aforementioned program can be stored and provided to a computer using any type of non-transitory computer readable media. Non-transitory computer readable media include any type of tangible storage media. Examples of non-transitory computer readable media include magnetic storage media (such as flexible disks, magnetic tapes, hard disk drives, etc.), optical magnetic storage media (e.g., magneto-optical disks), Compact Disc-Read Only Memory (CD-ROM), CD-Recordable (CD-R), CD-ReWritable (CD-R/W), and semiconductor memories (such as mask ROM, Programmable ROM (PROM), Erasable PROM (EPROM), flash ROM, Random Access Memory (RAM), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g., electric wires, and optical fibers) or a wireless communication line.

The main feature of this embodiment lies in the structure of controlling the pulling forces of the first pulling unit 35 and the second pulling unit 37 and known techniques can be used for the structure of controlling the operations of the walking assistance apparatus 2 and the treadmill 31. Therefore, in the following description, the structure of performing control of the pulling forces of the first pulling unit 35 and the second pulling unit 37 will be mainly described.

Figure 3:
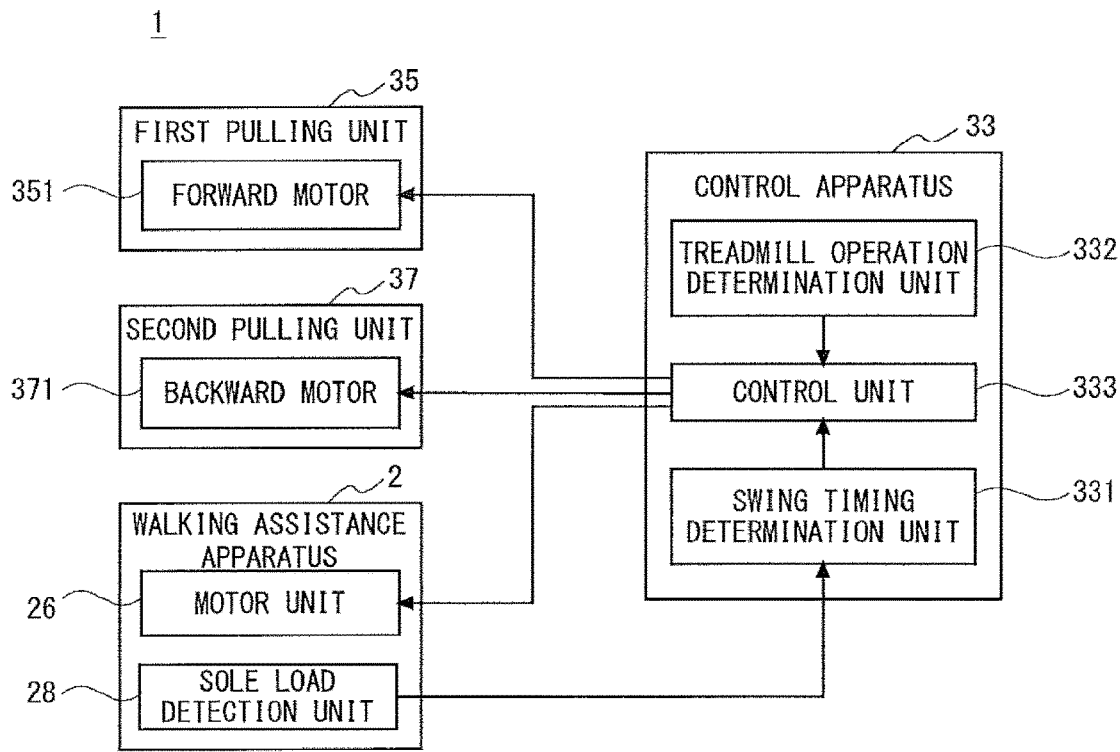
FIG. 3 is a block diagram showing one example of a schematic control block configuration of the walking training apparatus according to the embodiment of the present invention.

FIG. 3 is a block diagram showing one example of a schematic control block configuration of the walking training apparatus 1 according to this embodiment. The first pulling unit 35 includes the forward motor 351 described above and the second pulling unit 37 includes the backward motor 371 described above. The walking assistance apparatus 2 includes the motor unit 26 and the sole load detection unit 28 described above. The control apparatus 33 includes a swing timing determination unit 331, a treadmill operation determination unit 332, and a control unit (control means) 333. The swing timing determination unit 331, the treadmill operation determination unit 332, and the control unit 333 are achieved by the processor that executes the program stored in the storage unit.

The swing timing determination unit 331 determines, using the sole load detected by the sole load detection unit 28, a swing start timing, which is a timing when swing of the affected leg of the user on which the walking assistance apparatus 2 is mounted is started. In the following description, a period from the timing when the swing of the affected leg of the user is started to the timing when it ends (i.e., a period in which the affected leg of the user is in a lifted leg condition, which is a state in which it is floated from the floor) is called a swinging period. When the swing timing determination unit 331 determines the swing start timing, the swing timing determination unit 331 outputs an instruction for starting the swing to the control unit 333.

The following method may be employed, for example, as a method of determining the swing start timing.

A load threshold and an unload threshold (load threshold>unload threshold) are set in advance as thresholds of the sole load. Then the timing when the waveform of the sole load detected by the sole load detection unit 28 goes below the unload threshold for the first time after it exceeds the load threshold is determined to be the swing start timing.

The treadmill operation determination unit 332 determines whether the treadmill 31 is in an operating state (i.e., a state in which the belt 311 is being rotated) or a non-operating state (i.e., a state in which the rotation of the belt 311 is being stopped).

The following method may be employed, for example, as the method of determining the operating state of the treadmill 31.

(A) An operation start instruction button that instructs the start of the operation of the treadmill 31 and an operation end instruction button that instructs the end of the operation of the treadmill 31 are provided. Then the period from the timing when the operation start instruction button is pressed to the timing when the operation end instruction button is pressed is determined to be the period in which the treadmill 31 is in the operating state.

(B) An angle sensor that detects the angle of the rotation axis of the treadmill 31 is provided. When the angle of the rotation axis of the treadmill 31 detected by the angle sensor is changed to a predetermined threshold or more, it is determined that the treadmill 31 is in the operating state.

(C) One or more markers are arranged on the belt 311 of the treadmill 31 along the rotation direction and an imaging apparatus that captures images of the belt 311 in such a way that the marker(s) are included in the captured images is provided. Then the rotational speed of the belt

311 is determined based on the timing when the marker(s) appears on the images captured by the imaging apparatus. When the rotational speed of the belt 311 is equal to or larger than a predetermined threshold, it is determined that the treadmill 31 is in the operating state.

(D) An ammeter that measures the current flowing through a power supply cable of the treadmill 31 is provided. When the current value measured by the ammeter is not zero, it is determined that the treadmill 31 is in the operating state.

The control unit 333 controls the pulling forces of the first pulling unit 35 and the second pulling unit 37 in such a way as to reduce the load on the affected leg of the user. Further, the control unit 333 also controls the operation of the walking assistance apparatus 2.

Upon accepting the instruction for starting the swing from the swing timing determination unit 331, the control unit 333 brings the walking assistance apparatus 2 into the operating state (i.e., a state in which the knee joint part 22 is rotationally driven by the motor unit 26). During the swinging period, the user changes his/her knee from an extended condition to a flexed condition and then moves his/her knee back to the extended condition. Therefore, the control unit 333 brings the walking assistance apparatus 2 into the operating state and rotationally drives the knee joint part 22 by the motor unit 26 in such a way as to assist this user's motion.

Further, upon accepting the instruction for starting the swing from the swing timing determination unit 331, the control unit 333 determines whether the treadmill 31 is determined to be the operating state or the treadmill 31 is determined to be the non-operating state by the treadmill operation determination unit 332.

The control unit 333 determines, when the treadmill 31 is in the operating state, that the user is performing the walking operation and controls the pulling forces of the first pulling unit 35 and the second pulling unit 37 in such a way as to increase the force for lifting the walking assistance apparatus 2 upward. That is, the control unit 333 controls the pulling forces of the first pulling unit 35 and the second pulling unit 37 in such a way that a resultant pulling force, which is a resultant force of the pulling forces of the first pulling unit 35 and the second pulling unit 37, is directed upward. Accordingly, when the user performs the walking operation while the treadmill 31 is in the operating state, the load of the walking assistance apparatus 2 is relieved.

On the other hand, when the treadmill 31 is in the non-operating state, the control unit 333 determines that the user is performing the stepping operation on site and controls the pulling forces of the first pulling unit 35 and the second pulling unit 37 in such a way as to enhance the force for pulling the walking assistance apparatus 2 upward and to cause the pulling forces to be generated rearward as well. That is, the control unit 333 controls the pulling forces of the first pulling unit 35 and the second pulling unit 37 in such a way that the direction of the resultant pulling force, which is the resultant force of the pulling forces of the first pulling unit 35 and the second pulling unit 37, is changed rearward compared to the case in which the treadmill 31 is in the operating state. As a result, the resultant pulling force is directed upward and rearward. Accordingly, when the user performs the stepping operation while the treadmill 31 is in the non-operating state, it becomes easier for the user to bring back the affected leg rearward. Accordingly, it is possible to suppress the user from moving forward in accordance with the stepping operation, whereby it is possible to suppress the possibility that a burden is imposed on the user when the user performs the stepping operation.

The control unit 333 holds time-series patterns of the relief torque of the forward motor 351 and that of the backward motor 371 during the swinging period in each of the case in which the treadmill 31 is in the operating state and the case in which it is in the non-operating state. The time-series patterns are patterns in which, when the treadmill 31 is in the operating state, the relief torque of the forward motor 351 and that of the backward motor 371 are controlled in such a way that the resultant pulling force is directed upward during the swinging period. Further, when the treadmill 31 is in the non-operating state, the relief torque of the forward motor 351 and that of the backward motor 371 are controlled in such a way that the resultant pulling force is directed upward and rearward during the swinging period.

Therefore, upon accepting the instruction for starting the swing, the control unit 333 reads out the time-series patterns in accordance with the operating state or the non-operating state of the treadmill 31. Then the control unit 333 controls, during the following swinging period, the relief torque of the forward motor 351 and that of the backward motor 371 in accordance with the time-series patterns that have been read out, to thereby control the pulling forces of the first pulling unit 35 and the second pulling unit 37.

Figure 4:
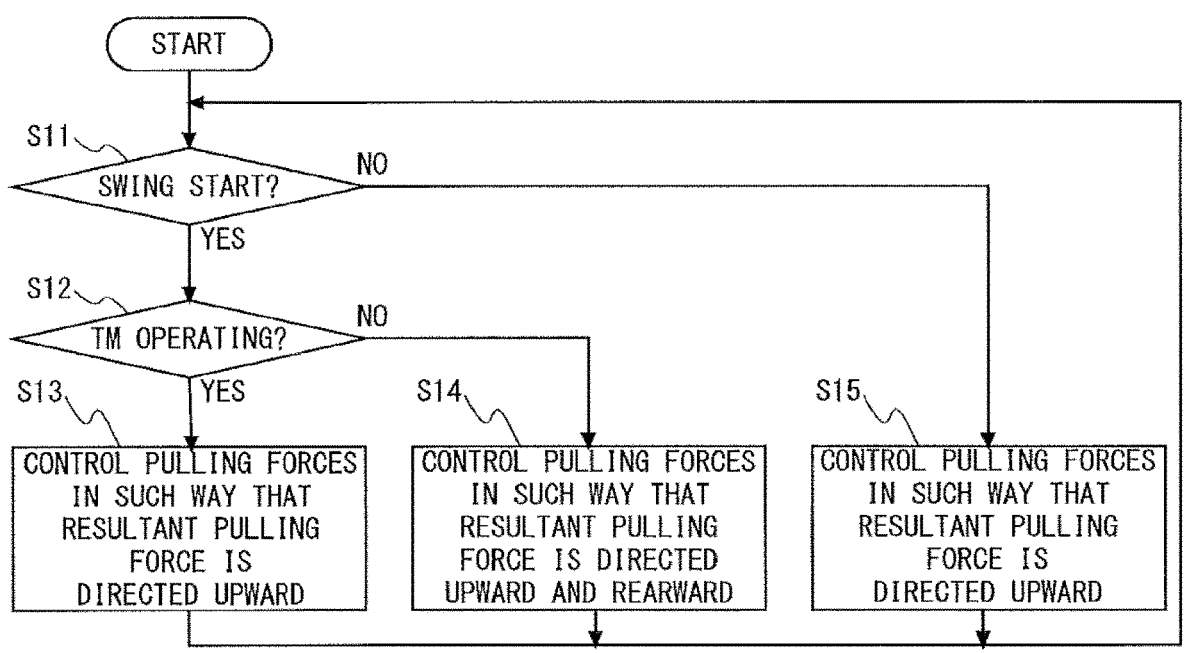
FIG. 4 is a flowchart showing one example of a schematic flow of a method of controlling the walking training apparatus according to the embodiment of the present invention.

FIG. 4 is a flowchart showing one example of a method of controlling the pulling forces of the first pulling unit 35 and the second pulling unit 37 in the control unit 333 of the walking training apparatus 1 according to this embodiment.

First, the control unit 333 determines whether it has accepted the instruction for starting the swing from the swing timing determination unit 331 (Step S11).

When the control unit 333 has accepted the instruction for starting the swing (YES in Step S11), the control unit 333 then brings the walking assistance apparatus 2 into the operating state and determines whether the treadmill operation determination unit 332 determines that the treadmill 31 is in the operating state or it determines that the treadmill 31 is in the non-operating state (Step S12).

When the treadmill 31 is in the operating state (YES in Step S12), the control unit 333 determines that the user is performing the walking operation and controls the pulling forces of the first pulling unit 35 and the second pulling unit 37 in such a way that the resultant pulling force, which is the resultant force of the pulling forces of the first pulling unit 35 and the second pulling unit 37, is directed upward (Step S13). Specifically, the control unit 333 reads out the time-series patterns of the relief torque of the forward motor 351 and that of the backward motor 371 during the swinging period in the state in which the treadmill 31 is in the operating state and controls, during the following swinging period, the relief torque of the forward motor 351 and that of the backward motor 371 in accordance with the time-series patterns that have been read out. In this way, during the swinging period, the resultant pulling force is directed upward.

On the other hand, when the treadmill 31 is in the non-operating state (NO in Step S12), the control unit 333 determines that the user is performing the stepping operation on site and controls the pulling forces of the first pulling unit 35 and the second pulling unit 37 in such a way that the resultant pulling force, which is the resultant force of the pulling forces of the first pulling unit 35 and the second pulling unit 37, is directed upward and rearward (Step S14). Specifically, the control unit 333 reads out the time-series patterns of the relief torque of the forward motor 351 and that of the backward motor 371 during the swinging period in the case in which the treadmill 31 is in the non-operating state and controls, during the following swinging period, the relief torque of the forward motor 351 and that of the backward motor 371 in accordance with the time-series patterns that have been read out. In this way, during the swinging period, the resultant pulling force is directed upward and rearward.

As described above, Steps S13 and S14 define the control of the forward motor 351 and the backward motor 371 during the swinging period. Therefore, the end of Steps S13 and S14 means the end of the swinging period. When the processes of Steps S13 and 14 are ended, that is, when the swinging period is ended, the process goes back to Step S11. When the control unit 333 has accepted the next instruction for starting the swing (YES in Step S11), the processes in Step S12 to S14 are performed. Therefore, Steps S11 to S14 are processes performed for each swinging period.

In a period other than the swinging period (i.e., a period in which the affected leg of the user is in a standing-leg state, which is a state in which it contacts the floor and this period will be hereinafter called a ground-contacting period), the control unit 333 does not accept the instruction for starting the swing (NO in Step S11). Therefore, the control unit 333 controls the pulling forces of the first pulling unit 35 and the second pulling unit 37 in such a way that the resultant pulling force, which is the resultant force of the pulling forces of the first pulling unit 35 and the second pulling unit 37 is directed upward (Step S15) The relief torque of the forward motor 351 and that of the backward motor 371 in Step S15 are the same as those in the ground-contacting period. During the ground-contacting period, the relief torque of the forward motor 351 and that of the backward motor 371 are substantially the same and have a predetermined fixed value.

In the following description, specific examples of the time-series patterns of the relief torque of the forward motor 351 and that of the backward motor 371 during the swinging period will be described.

(1) FIRST EXAMPLE

Figure 5:
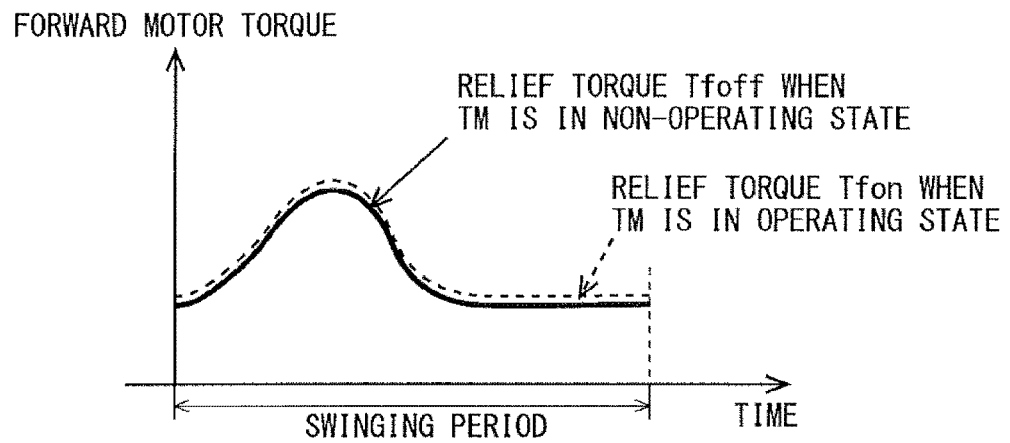
FIG. 5 is a diagram showing a first example of time-series patterns of relief torque of a forward motor and that of a backward motor in a swinging period in the walking training apparatus according to the embodiment of the present invention.
Figure 5:
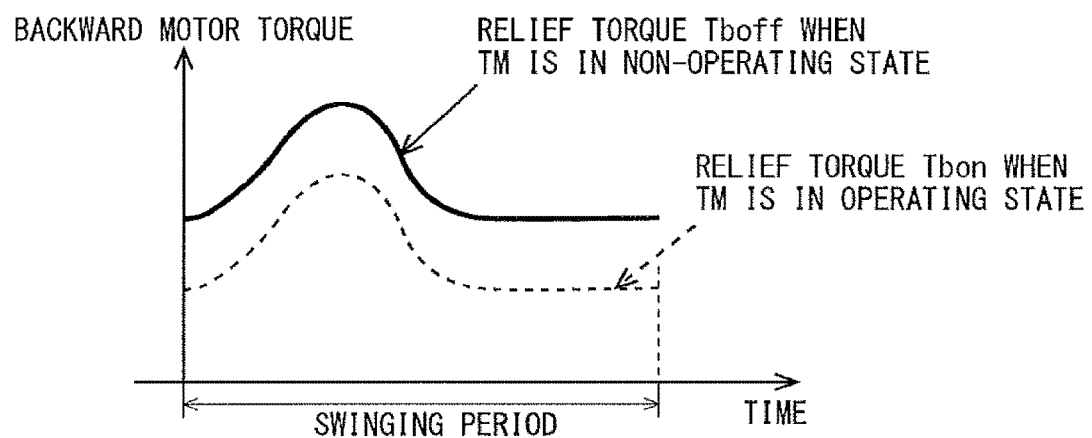

FIG. 5 is a diagram showing a first example of the time-series patterns of the relief torque of the forward motor 351 and that of the backward motor 371 during the swinging period.

The top view of FIG. 5 shows the time-series pattern of a relief torque Tfon of the forward motor 351 during the swinging period in the case in which the treadmill 31 is in the operating state (i.e., the time-series pattern of the relief torque of the forward motor 351 in Step S13 in FIG. 4) and the time-series pattern of a relief torque Tfoff of the forward motor 351 during the swinging period in the case in which the treadmill 31 is in the non-operating state (i.e., the time-series pattern of the relief torque of the forward motor 351 in Step S14 in FIG. 4). On the other hand, the bottom view of FIG. 5 shows the time-series pattern of a relief torque Tbon of the backward motor 371 during the swinging period in the case in which the treadmill 31 is in the operating state (i.e., the time-series pattern of the relief torque of the backward motor 371 in Step S13 in FIG. 4) and the time-series pattern of a relief torque Tboff of the backward motor 371 during the swinging period in the case in which the treadmill 31 is in the non-operating state (i.e., the time-series pattern of the relief torque of the backward motor 371 in Step S14 in FIG. 4) (the same is applicable to FIGS. 6 to 10 described below).

When the treadmill 31 is in the operating state at the time when the control unit 333 has accepted the instruction for starting the swing, as described above, the control unit 333 makes the resultant pulling force of the first pulling unit 35 and the second pulling unit 37 directed upward in such a way as to increase the force for pulling the walking assistance apparatus 2 upward.

In the first example, when the treadmill 31 is in the operating state at the time when the control unit 333 has accepted the instruction for starting the swing, the control unit 333 gradually increases the relief torque Tfon of the forward motor 351 and the relief torque Tbon of the backward motor 371 from the fixed value in the ground-contacting period and then returns it to the fixed value in the ground-contacting period. In this case, the relief torque Tfon and the relief torque Tbon are made substantially the same.

On the other hand, when the treadmill 31 is in the non-operating state at the time when the control unit 333 has accepted the instruction for starting the swing, as described above, the control unit 333 makes the resultant pulling force of the first pulling unit 35 and the second pulling unit 37 directed upward and rearward in such a way as to increase the force for pulling the walking assistance apparatus 2 upward and to cause the pulling forces to be generated rearward as well.

In the first example, when the treadmill 31 is in the non-operating state at the time when the control unit 333 has accepted the instruction for starting the swing, the control unit 333 uniformly makes, for the whole swinging period, the relief torque Tboff of the backward motor 371 larger than the relief torque Tbon of the backward motor 371 in the case in which the treadmill 31 is in the operating state. In this case, the relief torque Tfoff of the forward motor 351 is made substantially the same as the relief torque Tfon of the forward motor 351 in the case in which the treadmill 31 is in the operating state.

Accordingly, in the first example, when the treadmill 31 is in the non-operating state, for the whole swinging period, the resultant pulling force of the first pulling unit 35 and the second pulling unit 37 is directed upward and rearward. Therefore, when the user performs the stepping operation while the treadmill 31 is in the non-operating state, for the whole swinging period, the affected leg of the user can be pulled backward, whereby it is possible to suppress the user from moving forward in accordance with the stepping operation.

(2) SECOND EXAMPLE

Figure 6:
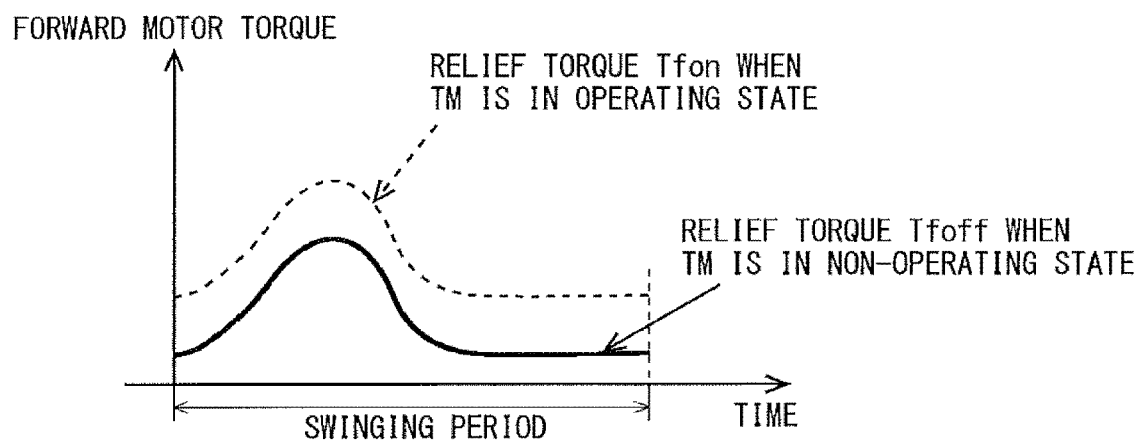
FIG. 6 is a diagram showing a second example of the time-series patterns of the relief torque of the forward motor and that of the backward motor in the swinging period in the walking training apparatus according to the embodiment of the present invention.
Figure 6:
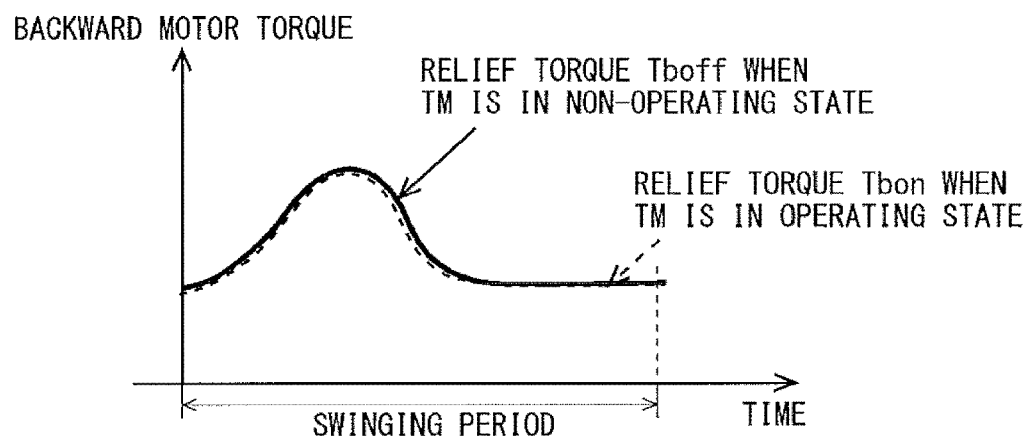

FIG. 6 is a diagram showing a second example of the time-series patterns of the relief torque of the forward motor 351 and that of the backward motor 371 during the swinging period.

In the second example, the relief torque Tfon of the forward motor 351 and the relief torque Tbon of the backward motor 371 during the swinging period in the case in which the treadmill 31 is in the operating state at the time when the control unit 333 has accepted the instruction for starting the swing are the same as those in the first example.

On the other hand, in the second example, when the treadmill 31 is in the non-operating state at the time when the control unit 333 has accepted the instruction for starting the swing, the control unit 333 uniformly makes, for the whole swinging period, the relief torque Tfoff of the forward motor 351 smaller than the relief torque Tfon of the forward motor 351 in the case in which the treadmill 31 is in the operating state. In this case, the relief torque Tboff of the backward motor 371 is made substantially the same as the relief torque Tbon of the backward motor 371 in the case in which the treadmill 31 is in the operating state.

Accordingly, in the second example, when the treadmill 31 is in the non-operating state, for the whole swinging period, the resultant pulling force of the first pulling unit 35 and the second pulling unit 37 is directed relatively upward and rearward. Therefore, when the user performs the stepping operation while the treadmill 31 is in the non-operating state, for the whole swinging period, the affected leg of the user can be pulled backward, whereby it is possible to suppress the user from moving forward in accordance with the stepping operation.

(3) THIRD EXAMPLE

Figure 7:
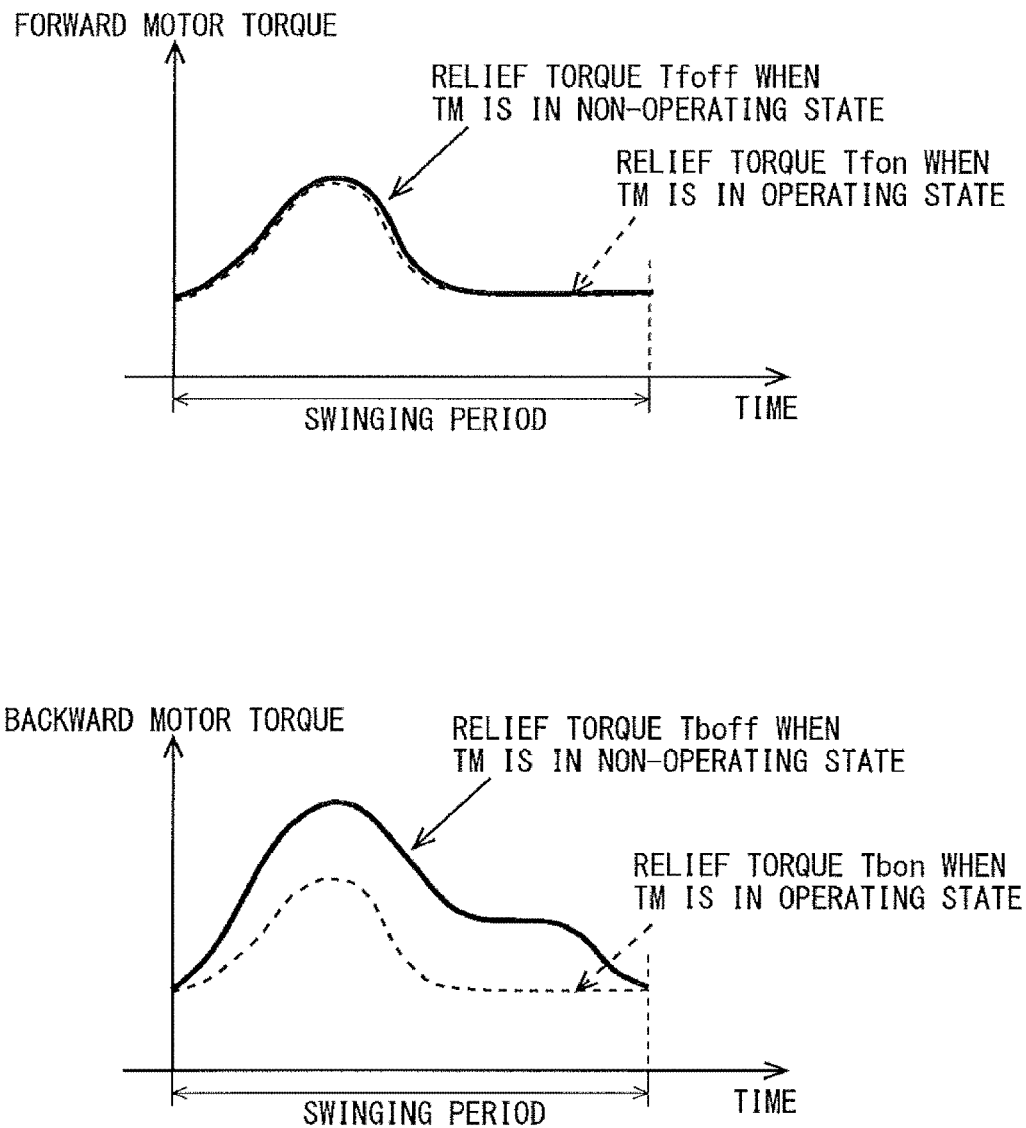
FIG. 7 is a diagram showing a third example of the time-series patterns of the relief torque of the forward motor and that of the backward motor in the swinging period in the walking training apparatus according to the embodiment of the present invention.

FIG. 7 is a diagram showing a third example of the time-series patterns of the relief torque of the forward motor 351 and that of the backward motor 371 during the swinging period.

In the third example, the relief torque Tfon of the forward motor 351 and the relief torque Tbon of the backward motor 371 during the swinging period in the case in which the treadmill 31 is in the operating state at the time when the control unit 333 has accepted the instruction for starting the swing are the same as those in the first example.

On the other hand, in the third example, when the treadmill 31 is in the non-operating state at the time when the control unit 333 has accepted the instruction for starting the swing, the control unit 333 makes the relief torque Tboff of the backward motor 371 larger than the relief torque Tbon of the backward motor 371 in the case in which the treadmill 31 is in the operating state, in the swinging period except for the timing when the swing is started and the swing is ended. The relief torque Tboff is set to a fixed value in the ground-contacting period when the swing is started and the swing is ended, similar to the relief torque Tbon. In this case, the relief torque Tfoff of the forward motor 351 is made substantially the same as the relief torque Tfon of the forward motor 351 when the treadmill 31 is in the operating state.

Accordingly, in the third example, when the treadmill 31 is in the non-operating state, in the swinging period except for the timing when the swing is started and the swing is ended, that is, in the period in which the affected leg of the user is actually in the lifted leg condition, the resultant pulling force of the first pulling unit 35 and the second pulling unit 37 is directed upward and rearward. Therefore, when the user performs the stepping operation while the treadmill 31 is in the non-operating state, in the period in which the affected leg of the user is actually in the lifted leg condition, the affected leg of the user can be pulled backward, whereby it is possible to suppress the user from moving forward in accordance with the stepping operation.

Further, the relief torque Tboff of the backward motor 371 is set to a fixed value in the ground-contacting period when the swing is started and the swing is ended. Accordingly, the relief torque of the backward motor 371 can be smoothly changed when the ground-contacting period is changed to the swinging period and the swinging period is changed to the ground-contacting period.

(4) FOURTH EXAMPLE

Figure 8:
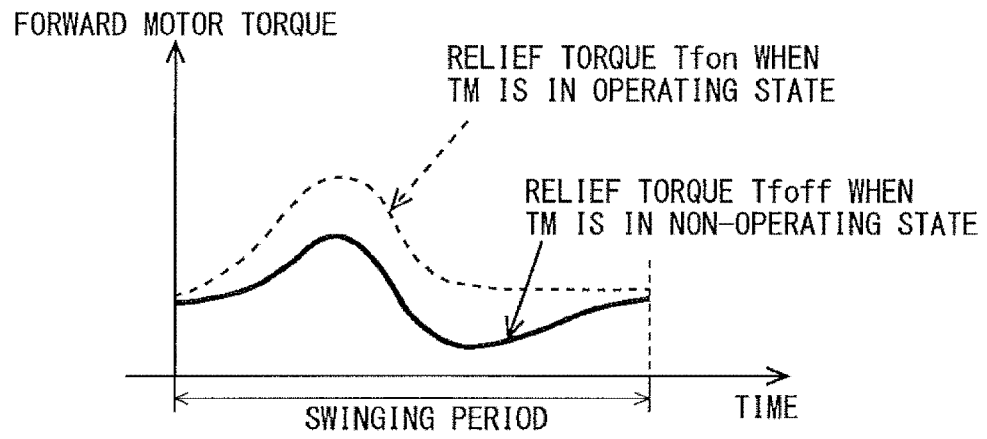
FIG. 8 is a diagram showing a fourth example of the time-series patterns of the relief torque of the forward motor and that of the backward motor in the swinging period in the walking training apparatus according to the embodiment of the present invention.
Figure 8:
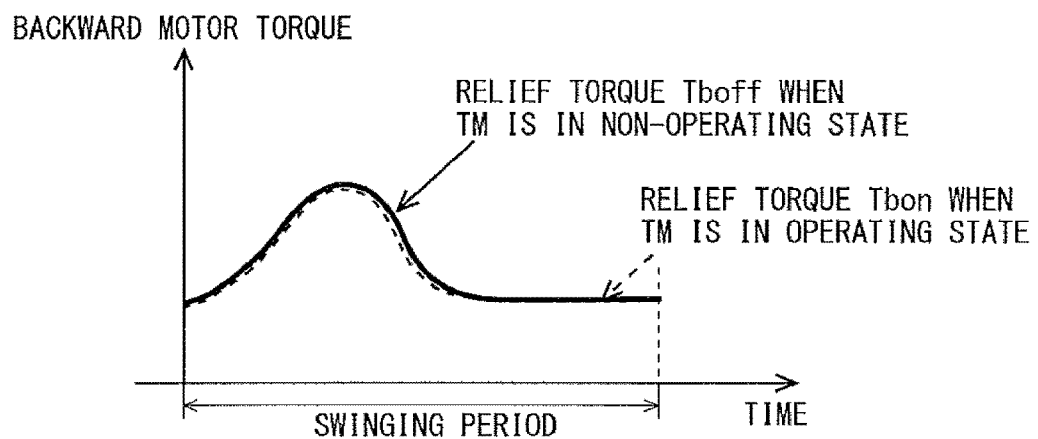

FIG. 8 is a diagram showing a fourth example of the time-series patterns of the relief torque of the forward motor 351 and that of the backward motor 371 during the swinging period.

In the fourth example, the relief torque Tfon of the forward motor 351 and the relief torque Tbon of the backward motor 371 during the swinging period in the case in which the treadmill 31 is in the operating state at the time when the control unit 333 has accepted the instruction for starting the swing are the same as those in the first example.

On the other hand, in the fourth example, when the treadmill 31 is in the non-operating state at the time when the control unit 333 has accepted the instruction for starting the swing, the control unit 333 makes the relief torque Tfoff of the forward motor 351 smaller than the relief torque Tfon of the forward motor 351 in the case in which the treadmill 31 is in the operating state, in the swinging period except for the timing when the swing is started and the swing is ended. The relief torque Tfoff is set to a fixed value in the ground-contacting period when the swing is started and the swing is ended, similar to the relief torque Tfon. In this case, the relief torque Tboff of the backward motor 371 is made substantially the same as the relief torque Tbon of the backward motor 371 in the case in which the treadmill 31 is in the operating state.

Accordingly, in the fourth example, when the treadmill 31 is in the non-operating state, in the swinging period except for the timing when the swing is started and the swing is ended, that is, in the period in which the affected leg of the user is actually in the lifted leg condition, the resultant pulling force of the first pulling unit 35 and the second pulling unit 37 is directed relatively upward and rearward. Therefore, when the user performs the stepping operation while the treadmill 31 is in the non-operating state, in the period in which the affected leg of the user is actually in the lifted leg condition, the affected leg of the user can be pulled backward, whereby it is possible to suppress the user from moving forward in accordance with the stepping operation.

Further, the relief torque Tfoff of the forward motor 351 is set to a fixed value in the ground-contacting period when the swing is started and the swing is ended. Accordingly, the relief torque of the forward motor 351 can be smoothly changed when the ground-contacting period is changed to the swinging period and the swinging period is changed to the ground-contacting period.

(5) FIFTH EXAMPLE

Figure 9:
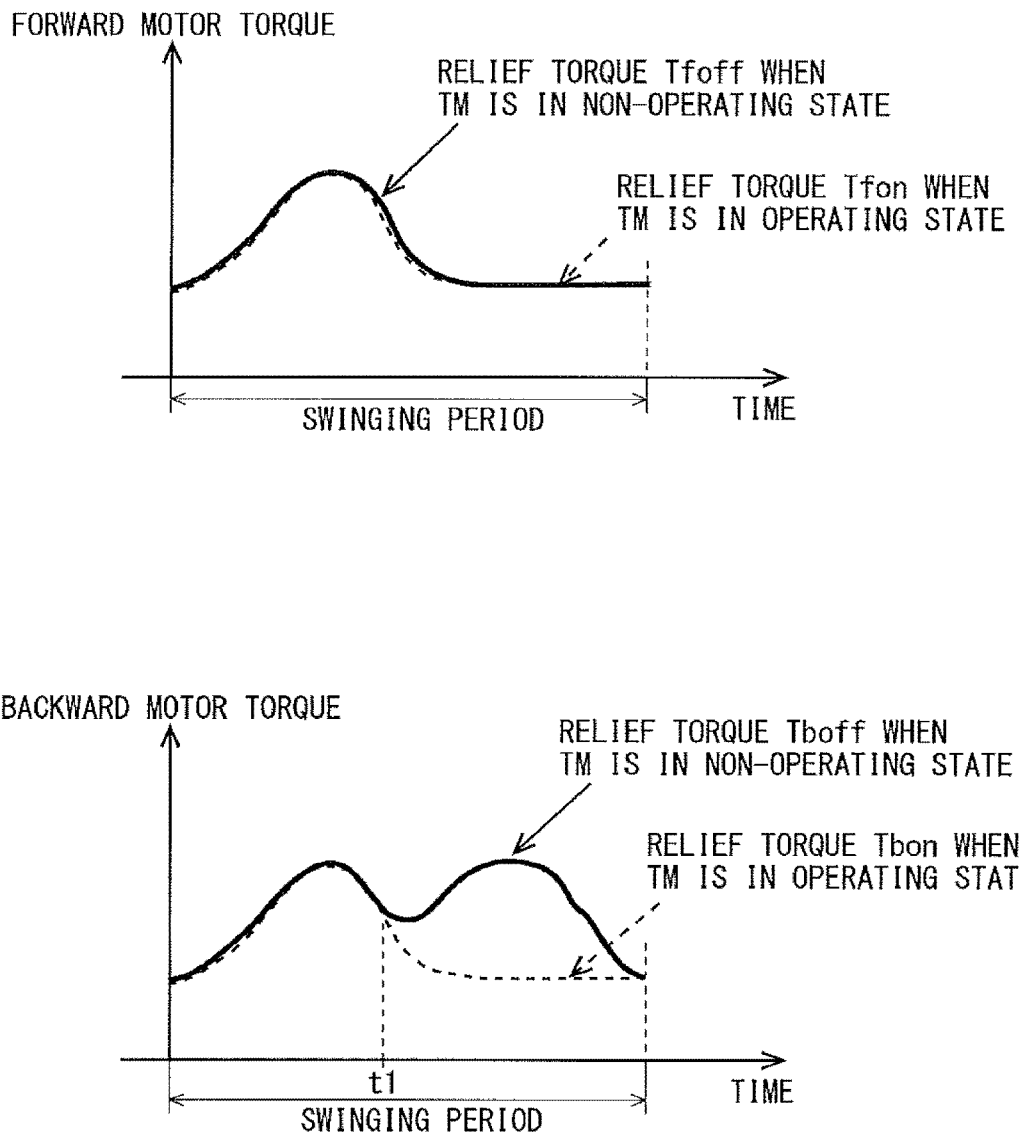
FIG. 9 is a diagram showing a fifth example of the time-series patterns of the relief torque of the forward motor and that of the backward motor in the swinging period in the walking training apparatus according to the embodiment of the present invention.

FIG. 9 is a diagram showing a fifth example of the time-series patterns of the relief torque of the forward motor 351 and that of the backward motor 371 during the swinging period.

In the fifth example, the relief torque Tfon of the forward motor 351 and the relief torque Tbon of the backward motor 371 during the swinging period in the case in which the treadmill 31 is in the operating state at the time when the control unit 333 has accepted the instruction for starting the swing are the same as those in the first example.

On the other hand, in the fifth example, when the treadmill 31 is in the non-operating state at the time when the control unit 333 has accepted the instruction for starting the swing, the control unit 333 makes the relief torque Tboff of the backward motor 371 larger than the relief torque Tbon of the backward motor 371 in the case in which the treadmill 31 is in the operating state, in a period after a predetermined time position t1 during the swinging period. When the swing is started and the swing is ended, the relief torque Tboff is set to a fixed value in the ground-contacting period, similar to the relief torque Tbon. In this case, the relief torque Tfoff of the forward motor 351 is made substantially the same as the relief torque Tfon of the forward motor 351 in the case in which the treadmill 31 is in the operating state.

Accordingly, in the fifth example, when the treadmill 31 is in the non-operating state, in the period after the predetermined time position t1 during the swinging period, the resultant pulling force of the first pulling unit 35 and the second pulling unit 37 is directed upward and rearward. Therefore, when the user performs the stepping operation while the treadmill 31 is in the non-operating state, the affected leg of the user can be pulled backward at least just before the affected leg of the user contacts the floor, whereby it is possible to suppress the user from moving forward in accordance with the stepping operation.

While the predetermined time position t1 is set to substantially the center of the swinging period and the relief torque Tboff is made larger than the relief torque Tbon in the latter part of the swinging period in FIG. 9, this configuration is merely an example. In the fifth example, it is sufficient that the relief torque Tboff be larger than the relief torque Tbon just before the swing is ended. Therefore, the predetermined time position t1 may be before or after substantially the center of the swinging period.

Further, while the relief torque Tboff is set to a fixed value in the ground-contacting period when the swing is ended, similar to the relief torque Tbon, in FIG. 9, this configuration is merely an example. In the fifth example, the relief torque Tboff may be made larger than the relief torque Tbon also when the swing is ended.

(6) SIXTH EXAMPLE

Figure 10:
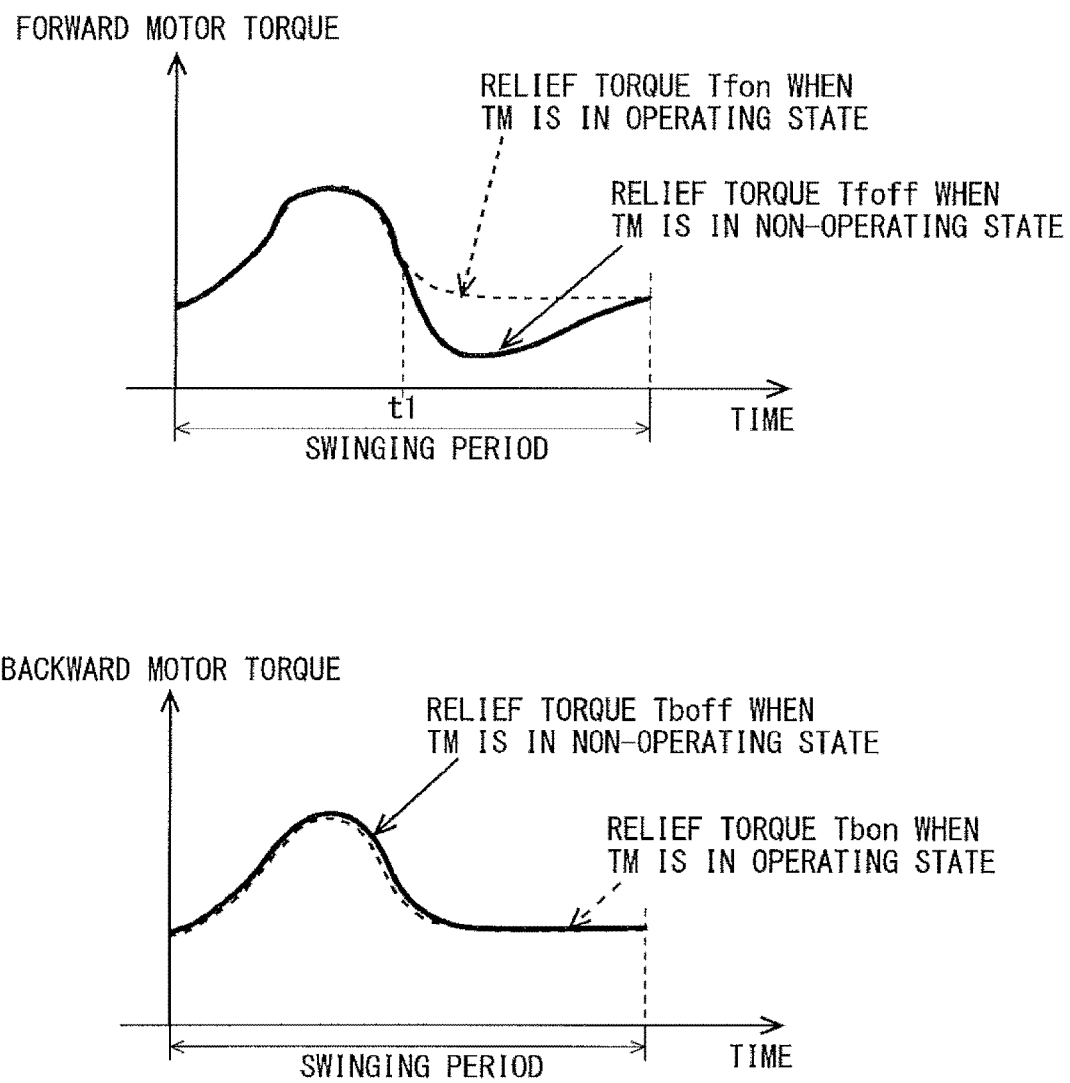
FIG. 10 is a diagram showing a sixth example of the time-series patterns of the relief torque of the forward motor and that of the backward motor in the swinging period in the walking training apparatus according to the embodiment of the present invention.

FIG. 10 is a diagram showing a sixth example of the time-series patterns of the relief torque of the forward motor 351 and that of the backward motor 371 during the swinging period.

In the sixth example, the relief torque Tfon of the forward motor 351 and the relief torque Tbon of the backward motor 371 during the swinging period in the case in which the treadmill 31 is in the operating state at the time when the control unit 333 has accepted the instruction for starting the swing are similar to those in the first example.

On the other hand, in the sixth example, when the treadmill 31 is in the non-operating state at the time when the control unit 333 has accepted the instruction for starting the swing, the control unit 333 makes the relief torque Tfoff of the forward motor 351 smaller than the relief torque Tfon of the forward motor 351 in the case in which the treadmill 31 is in the operating state, in the period after the predetermined time position t1 during the swinging period. The relief torque Tfoff is set to a fixed value in the ground-contacting period when the swing is started and the swing is ended, similar to the relief torque Tfon. In this case, the relief torque Tboff of the backward motor 371 is made substantially the same as the relief torque Tbon of the backward motor 371 in the case in which the treadmill 31 is in the operating state.

Accordingly, in the sixth example, when the treadmill 31 is in the non-operating state, in the period after the predetermined time position t1 during the swinging period, the resultant pulling force of the first pulling unit 35 and the second pulling unit 37 is directed relatively upward and rearward. Therefore, when the user performs the stepping operation while the treadmill 31 is in the non-operating state, the affected leg of the user can be pulled backward at least just before the affected leg of the user contacts the floor, whereby it is possible to suppress the user from moving forward in accordance with the stepping operation.

While the predetermined time position t1 is set to substantially the center of the swinging period and the relief torque Tfoff is made smaller than the relief torque Tfon in the latter part of the swinging period in FIG. 10, this configuration is merely an example. In the sixth example, it is sufficient that the relief torque Tfoff be smaller than the relief torque Tfon immediately before the swing is ended. Therefore, the predetermined time position t1 may be before or after the substantially the center of the swinging period.

Further, while the relief torque Tfoff is set to a fixed value in the ground-contacting period when the swing is ended, similar to the relief torque Tfon, in FIG. 10, this configuration is merely an example. In the sixth example, the relief torque Tfoff may be made smaller than the relief torque Tfon also when the swing is ended.

As described above, according to this embodiment, the control unit 333 controls, when the treadmill 31 is in the non-operating state, the pulling forces of the first pulling unit 35 and the second pulling unit 37 in such a way that the resultant pulling force, which is the resultant force of the pulling forces of the first pulling unit 35 and the second pulling unit 37, is changed backward compared to the case in which the treadmill 31 is in the operating state. Therefore, when the user performs the stepping operation while the treadmill 31 is in the non-operating state, it becomes easier for the user to bring back the affected leg rearward. Accordingly, it is possible to suppress the user from moving forward in accordance with the stepping operation, whereby it is possible to suppress the possibility that a burden is imposed on the user when the user performs the stepping operation.

Further, according to this embodiment, the control unit 333 controls, when the treadmill 31 is in the non-operating state in the state in which the walking assistance apparatus 2 is in the operating state, the pulling forces of the first pulling unit 35 and the second pulling unit 37 in such a way that the resultant pulling force, which is the resultant force of the pulling forces of the first pulling unit 35 and the second pulling unit 37, is changed rearward compared to the case in which the treadmill 31 is in the operating state. Accordingly, it is possible to suppress the possibility that a burden is imposed on the user while the user is performing the stepping operation, which is close to the walking operation for operating the walking assistance apparatus 2.

Note that the present invention is not limited to the aforementioned embodiment and may be changed as appropriate without departing from the spirit of the present invention.

For example, in the aforementioned embodiment, the walking assistance apparatus is in the operating state at the time when the instruction for starting the swing has been accepted. Therefore, the stepping operation is performed while the walking assistance apparatus is in the operating state. However, this is merely an example. The stepping operation may be performed while the walking assistance apparatus is in the non-operating state. In this case, the walking assistance apparatus is brought into the operating state only during the walking operation. Therefore, the timing when the walking assistance apparatus is brought into the operating state may be a timing when it is determined that the treadmill is in the operating state after the instruction for starting the swing has been accepted.

Further, while only one pattern of the length of the swinging period is shown in the aforementioned embodiment, it can be considered that the length of the swinging period varies among individuals. Therefore, it may be possible to set the length of the swinging period for each user and set the time-series patterns in accordance with the length of the swinging period.

Further, while the pulling forces of the first and second pulling units are controlled by adjusting the relief torque of the motors in the aforementioned embodiment, this is merely an example. For example, the first and second pulling units may include spring members connected to the respective wires and the pulling forces of the first and second pulling units may be controlled by adjusting the elastic forces of the spring members.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A walking training apparatus comprising:
   a treadmill;
   a walking assistance apparatus including a frame configured to be mounted on a leg part of a user and assist the user's walking;
   a first pulling unit including a first motor, the first pulling unit configured to pull at least one of the walking assistance apparatus and the leg part of the user on which the walking assistance apparatus is mounted upward and frontward;
   a second pulling unit including a second motor, the second pulling unit configured to pull at least one of the walking assistance apparatus and the leg part of the user on which the walking assistance apparatus is mounted upward and rearward; and
   an electronic control unit configured to:
      determine whether the treadmill is an operation state in which the treadmill is rotating or in a non-operation state in which the treadmill is stopped,
      control pulling forces of the first pulling unit and the second pulling unit in such a way as to reduce a load applied to the leg part of the user on which the walking assistance apparatus is mounted,
      when a determination of the operation state is made, control pulling forces of the first pulling unit and the second pulling unit in such a way that a direction of a resultant pulling force, which is a resultant force of the pulling force of the first pulling unit and the pulling force of the second pulling unit, is upward, and
      when a determination of the non-operation state is made, control the pulling forces of the first pulling unit and the second pulling unit in such a way that the direction of the resultant pulling force is upward and rearward.

2. A method of controlling a walking training apparatus, the walking training apparatus comprising a treadmill, a walking assistance apparatus including a frame configured to be mounted on a leg part of a user and assist the user's walking, a first pulling unit including a first motor, the first pulling unit configured to pull at least one of the walking assistance apparatus and the leg part of the user on which the walking assistance apparatus is mounted upward and frontward, and a second pulling unit including a second motor, the second pulling unit configured to pull at least one of the walking assistance apparatus and the leg part of the user on which the walking assistance apparatus is mounted upward and rearward, the method comprising:
   determining with an electronic control device whether the treadmill is an operation state in which the treadmill is rotating or in a non-operation state in which the treadmill is stopped,
   controlling with the electronic control device pulling forces of the first pulling unit and the second pulling unit in such a way as to reduce a load applied to the leg part of the user on which the walking assistance apparatus is mounted,
   when a determination of the operation state is made, controlling pulling forces of the first pulling unit and the second pulling, unit in such a way that a direction of a resultant pulling force, which is a resultant force of the pulling, force of the first pulling unit and the pulling, force of the second pulling unit, is upward, and
   when a determination of the non-operation state is made, controlling the pulling forces of the first pulling unit and the second pulling unit in such a way that the direction of the resultant pulling force is upward and rearward.

\* \* \* \* \*